(12) United States Patent
Stangenes et al.

(10) Patent No.: US 8,206,385 B2
(45) Date of Patent: Jun. 26, 2012

(54) CATHETER ASSEMBLY WITH FRONT-LOADED TIP AND MULTI-CONTACT CONNECTOR

(75) Inventors: Todd Raymond Stangenes, Minneapolis, MN (US); Clinton Schneider, Plymouth, MN (US); Richard Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 664 days.

(21) Appl. No.: 12/347,578

(22) Filed: Dec. 31, 2008

(65) Prior Publication Data

US 2009/0306655 A1 Dec. 10, 2009

Related U.S. Application Data

(63) Continuation-in-part of application No. 12/135,685, filed on Jun. 9, 2008.

(51) Int. Cl.
*A61B 18/18* (2006.01)
(52) U.S. Cl. ............................. 606/41; 606/32
(58) Field of Classification Search .................. 606/32, 606/34, 41, 42
See application file for complete search history.

(56) References Cited

U.S. PATENT DOCUMENTS

| | | |
|---|---|---|
| 4,641,649 A | 2/1987 | Walinsky et al. |
| 5,297,549 A | 3/1994 | Beatty et al. |
| 5,311,866 A | 5/1994 | Kagan et al. |
| 5,341,807 A | 8/1994 | Nardella |
| 5,429,131 A | 7/1995 | Scheinman et al. |
| 5,447,529 A | 9/1995 | Marchlinski et al. |
| 5,562,721 A | 10/1996 | Marchlinski et al. |
| 5,673,704 A | 10/1997 | Marchlinski et al. |
| 5,697,377 A | 12/1997 | Wittkampf |

(Continued)

FOREIGN PATENT DOCUMENTS

WO 2007067941 A2 6/2007

OTHER PUBLICATIONS

Cho, Sungbo et al., "Design of electrode array for impedance measurement of lesions in arteries", 2005 Physiol. Meas. 26 S19-26.

(Continued)

*Primary Examiner* — Laura Bouchelle
(74) *Attorney, Agent, or Firm* — Dykema Gossett PLLC

(57) ABSTRACT

The invention is directed to a catheter suitable for medical procedures such as cardiac ablation. The catheter includes a front-loaded catheter tip with an electrically active element. The catheter can include an elongate catheter shaft assembly having an inner shaft member with a distal end and a proximal end, and an outer shaft member with a distal end, a proximal end, and a lumen between the distal end and the proximal end. The inner shaft member can be inserted into the lumen of the outer shaft member along a longitudinal direction. The inner shaft member can include, at the distal end, a catheter tip member having a lateral dimension that is larger than a lateral dimension of the lumen of the outer shaft member. The catheter tip member includes at least one electrically active element, and the proximal end of the inner shaft member has at least one electrode disposed on the external surface of the shaft member, such that when inserted into a handle, the electrode electrically contacts an electrical connector element.

22 Claims, 11 Drawing Sheets

U.S. PATENT DOCUMENTS

| | | |
|---|---|---|
| 5,718,241 A | 2/1998 | Ben-Haim et al. |
| 5,814,043 A * | 9/1998 | Shapeton ............... 606/48 |
| 5,836,990 A | 11/1998 | Li |
| 5,837,001 A | 11/1998 | Mackey |
| 5,954,665 A | 9/1999 | Ben-Haim |
| 6,063,078 A | 5/2000 | Wittkampf |
| 6,217,576 B1 * | 4/2001 | Tu et al. ............... 606/41 |
| 6,226,542 B1 | 5/2001 | Reisfeld |
| 6,256,540 B1 | 7/2001 | Panescu et al. |
| 6,443,894 B1 | 9/2002 | Sumanaweera et al. |
| 6,471,693 B1 | 10/2002 | Carroll et al. |
| 6,690,963 B2 | 2/2004 | Ben-Haim et al. |
| 6,965,795 B2 | 11/2005 | Rock |
| 7,263,397 B2 | 8/2007 | Hauck et al. |
| 7,776,034 B2 * | 8/2010 | Kampa ............... 606/41 |
| 2001/0039413 A1 | 11/2001 | Bowe |
| 2001/0047129 A1 | 11/2001 | Hall et al. |
| 2002/0049375 A1 | 4/2002 | Strommer et al. |
| 2003/0045871 A1 | 3/2003 | Jain et al. |
| 2003/0093067 A1 | 5/2003 | Panescu et al. |
| 2007/0073179 A1 | 3/2007 | Afonso et al. |
| 2007/0100332 A1 | 5/2007 | Paul et al. |
| 2007/0123764 A1 | 5/2007 | Thao et al. |
| 2007/0244479 A1 | 10/2007 | Beatty et al. |
| 2007/0255162 A1 | 11/2007 | Abboud et al. |
| 2008/0091169 A1 | 4/2008 | Heideman et al. |
| 2008/0091193 A1 | 4/2008 | Kauphusman et al. |
| 2008/0132890 A1 | 6/2008 | Woloszko et al. |
| 2008/0234564 A1 | 9/2008 | Beatty et al. |

OTHER PUBLICATIONS

Fenici, R. R. et al., "Biomagnetically localizable multipurpose catheter and method for MCG guided intracardiac electrophysiology, biopsy and ablation of cardiac arrhythmias", Int'l Journal of Cardiac Imaging 7; 207-215, 1991.

Gales, Rosemary et al., "Use of bioelectrical impedance analysis to assess body composition of seals", Ocean Sciences Center, Memorial University of Newfoundland, 1992.

Masse, Stephane et al., "A Three-dimensional display for cardiac activation mapping", PACE, vol. 14, Apr. 1991.

Salazar, Y et al., "Transmural versus nontransmural in situ electrical impedance spectrum for healthy, ischemic, and healed myocardium", Biomedical Engineering, Aug. 2004.

* cited by examiner

CATHETER ASSEMBLY WITH FRONT-LOADED TIP AND MULTI-CONTACT CONNECTOR

RELATED APPLICATIONS

The present application is a continuation-in-part of U.S. patent application Ser. No. 12/135,685 for CATHETER ASSEMBLY WITH FRONT LOADED TIP, filed Jun. 9, 2008, which is hereby incorporated by reference as though fully set forth herein.

BACKGROUND OF THE INVENTION a. Field of the Invention

The instant invention relates to a catheter assembly with a front-loaded catheter tip and having a multi-contact connector. In particular, the instant invention relates to catheters comprising multi-contact connectors at the proximal end that allow for electrical connections in constrained spaces.

b. Background Art

It is known that catheters are widely used to perform a variety of functions relating to therapeutic and diagnostic medical procedures involving tissues within a body. For example, catheters can be inserted within a vessel located near the surface of a body (e.g., in an artery or vein in the leg, neck, or arm) and maneuvered to a region of interest within the body to enable diagnosis and/or treatment of tissue without the need for more invasive procedures. For example, catheters can be inserted into a body during ablation and mapping procedures performed on tissue within a body. Tissue ablation can be accomplished using a catheter to apply localized radiofrequency (RF) energy to a selected location within the body to create thermal tissue necrosis. Typically, the ablation catheter is inserted into a vessel in the body, sometimes with the aid of a pull wire or introducer, and threaded through the vessel until a distal tip of the ablation catheter reaches the desired location for the procedure involving a body tissue. The ablation catheters commonly used to perform these ablation procedures produce lesions and electrically isolate or render the tissue non-contractile at various points in the cardiac tissue by physical contact of the cardiac tissue with an electrode of the ablation catheter and application of energy, such as RF energy. By way of further example, another procedure, mapping, uses a catheter with sensing electrodes to monitor various forms of electrical activity in the body.

Known ablation catheter assemblies typically involve insertion of a catheter through a sheath or introducer where the standard catheter shaft size is 7 FR (French), the standard catheter tip size is 4-8 FR, and the standard sheath or introducer size is 8-11 FR. For purposes of this application, the term "FR (French)" means the French catheter scale used to measure the outer diameter of catheters. In the French gauge system as it is also known, the diameter in millimeters of the catheter can be determined by dividing the French size by three. Thus, an increasing French size corresponds with a larger diameter catheter. Typically, the outer diameter of the sheath or introducer is larger than the outer diameter of the catheter shaft and is also larger than the outer diameter of the catheter tip. A difficulty in obtaining an adequate ablation lesion using known ablation catheter assemblies for certain procedures is that conventional catheter assemblies have overall a large outer diameter that can potentially cause trauma. For instance, when performing transseptal catheterization or punctures across the septum of the heart, the fossa ovalis can be susceptible to trauma or injury. It is possible that, using known devices, two, three, or more transseptal punctures can have to be made through the same area of the fossa ovalis to get more of the catheter assembly from one side of the heart to the other side of the heart.

Another difficulty with known catheter assemblies such as those used for ablation procedures is that the ability to freely manipulate the catheter within the sheath or introducer is compromised or decreased because the catheter has greater overall contact with the interior walls of the sheath or introducer, as the standard catheter used for ablation normally has a constant diameter from the distal tip to the proximal handle end. Typically, the catheter and catheter tip is a single unitary assembly of constant diameter along the entire length of the catheter assembly, and typically, the sheath or introducer has a constant outer diameter and constant inner diameter along the entire length of the catheter assembly. When there is greater contact between the catheter and sheath or introducer, there is less degree of freedom of movement available in using the catheter assembly through transseptal punctures.

Another difficulty with known catheter assemblies such as those used for ablation procedures is that the catheter tips can not be of a large enough size to accommodate an electrically active element or to accommodate magnetic material to create a magnetic field, so that the magnetized catheter can be pulled and guided through the body and through the heart rather than pushed. Known catheter assemblies with magnetized elements often cannot accommodate a large enough magnetic material or element to create a magnetic field or they create unfavorable drag forces inside the catheter or sheath.

Known catheter assemblies such as those used for ablation procedures, include a standard electrical connector at their proximal end. These designs facilitate a connection between the catheter electrode wires and a multi-pin connector that is outside of a patient's body. Often the size of this connection is unimportant in most catheter assemblies; however, when the size of the connection is constrained, the electrical connector is more difficult to accommodate. This challenge is further exacerbated when the catheter assembly is irrigated, which adds the complicating element of a fluid lumen connection.

Accordingly, there remains a need for a catheter assembly that can be used for medical procedures such as ablation that addresses these issues and that will minimize and/or eliminate one or more of the above-identified deficiencies.

BRIEF SUMMARY OF THE INVENTION

It is desirable to provide a catheter that can be used for medical procedures such as ablation that has an enlarged catheter tip with an electrically active element, that has a smaller diameter shaft than known catheter assemblies, and that minimizes or eliminates trauma to regions of the heart that could potentially be caused by known catheter assemblies during transseptal punctures or procedures. Typically, the smaller the transseptal punctures that are made, the less trauma that results to the heart. It is further desirable to provide a catheter that can be used for medical procedures such as ablation that has the ability to be freely manipulated with less contact to the interior walls of the sheath or introducer and that has the ability to be more freely movable through transseptal punctures. It is further desirable to provide a catheter that can be used for medical procedures such as ablation that has a catheter tip with a maximum outer diameter that is equal to the outer diameter of the outer shaft member of the catheter.

The instant invention is directed to an ablation catheter assembly with a front-loaded catheter tip. In one embodiment, a catheter is provided comprising: an elongate catheter shaft assembly including an inner shaft member having a distal end and a proximal end, and an outer shaft member having a distal end, a proximal end, and a lumen between the distal end and the proximal end thereof, the inner shaft member being inserted into the lumen of the outer shaft member along a longitudinal direction of the elongate catheter shaft assembly, wherein the inner shaft member includes at the distal end thereof a catheter tip member having a lateral dimension that is larger than a lateral dimension of the lumen of the outer shaft member, and wherein the catheter tip member includes at least one electrically active element.

In another embodiment, a catheter is provided comprising: an elongate catheter shaft assembly including an inner shaft member having a distal end and a proximal end, and an outer shaft member having a distal end, a proximal end, and a lumen between the distal end and the proximal end thereof, the inner shaft member being inserted into the lumen of the outer shaft member along a longitudinal direction of the elongate catheter shaft assembly, the inner shaft member extending at least substantially through an entire length of the lumen of the outer shaft member, wherein the inner shaft member includes at the distal end thereof a catheter tip member having a lateral dimension that is larger than a lateral dimension of a lumen of the outer shaft member, an electrical connector disposed at a proximal end of the elongate catheter shaft assembly; and an electrical line coupled between the electrical connector and the catheter tip member.

In another embodiment, a catheter is provided comprising: an elongate catheter shaft assembly including an inner shaft member having a distal end and a proximal end, and an outer shaft member having a distal end, a proximal end, and a lumen between the distal end and the proximal end thereof, the inner shaft member being inserted into the lumen of the outer shaft member along a longitudinal direction of the elongate catheter shaft assembly, wherein the inner shaft member includes at the distal end thereof a catheter tip member having a lateral dimension that is larger than a lateral dimension of the lumen of the outer shaft member, wherein the catheter tip member includes at least one electrically active element, and wherein the inner shaft member including the catheter tip member is inserted into the lumen from the distal end of the outer shaft member to be detachably connected to the outer shaft member, and is removable out of the lumen from the distal end of the outer shaft member.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Figure 1:
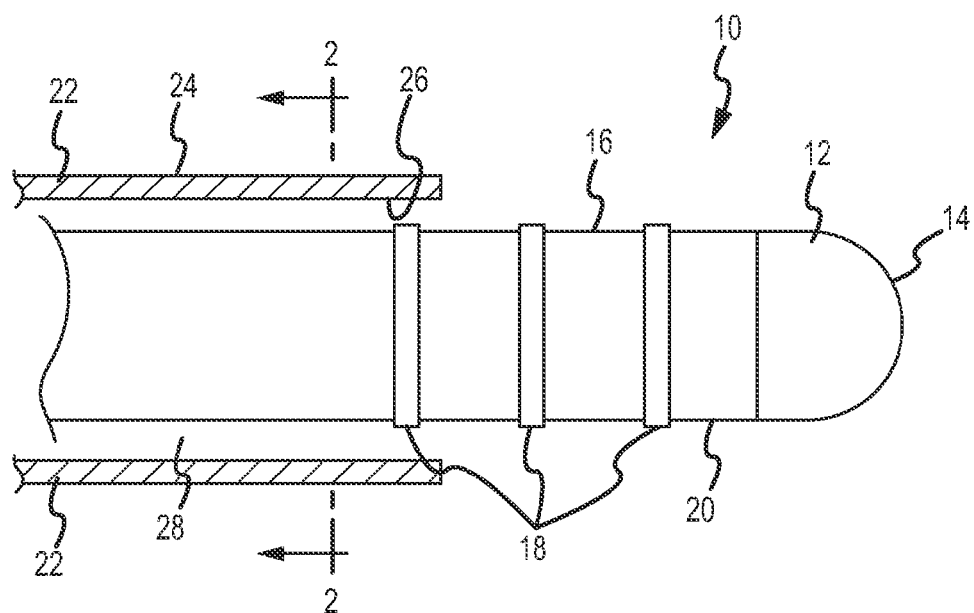
FIG. 1 is a fragmentary view in partial cross-section of a prior art ablation catheter assembly.
Figure 2:
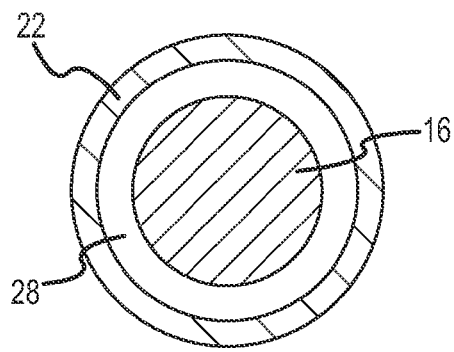
FIG. 2 is a cross-sectional view, taken along line 2-2 of FIG. 1, of the catheter and sheath of FIG. 1.
Figure 3:
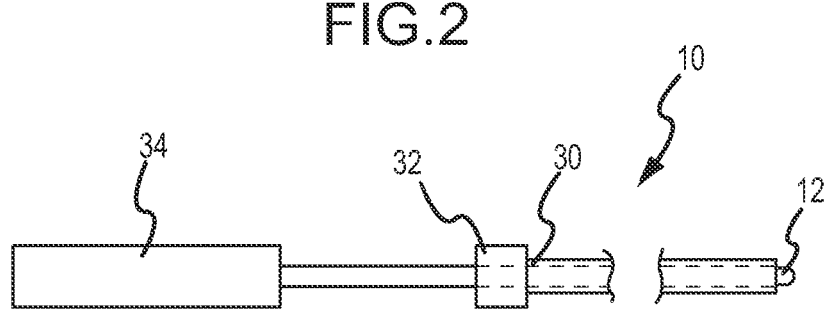
FIG. 3 is a fragmentary view of the ablation catheter assembly of FIG. 1 showing a proximal end of the catheter assembly.

Referring now to the figures, FIG. 1 is a fragmentary view in partial cross-section of a prior art catheter assembly 10 that can be used for medical procedures such as ablation procedures. The catheter assembly 10 includes a catheter tip 12 at a distal end 14, a catheter shaft 16 having a plurality of electrode rings 18 around the circumference of the shaft at a shaft distal end 20, a sheath 22 having an outer surface 24 and an inner surface 26, and a lumen 28. Typically, the catheter shaft is advanced through the sheath. Typically, the size of the catheter tip is 7 FR (French) to 7.5 FR. FIG. 2 is a cross-sectional view, taken along line 2-2 of FIG. 1, of the catheter shaft 16, sheath 22, and lumen 28. The outer diameter of the sheath and inner diameter of the sheath are both larger than the outer diameters of the shaft 16 and the tip 12. FIG. 3 is a fragmentary view of the catheter assembly 10 of FIG. 1. The catheter assembly includes a proximal end 30 with a connector member 32 and a handle 34. The connector member 32 can comprise a standard grounding pad, quick connect, spring-loaded contact, clamp connect, or another type of electrical connector suitable for use with catheters such as ablation catheters.

Figure 4:
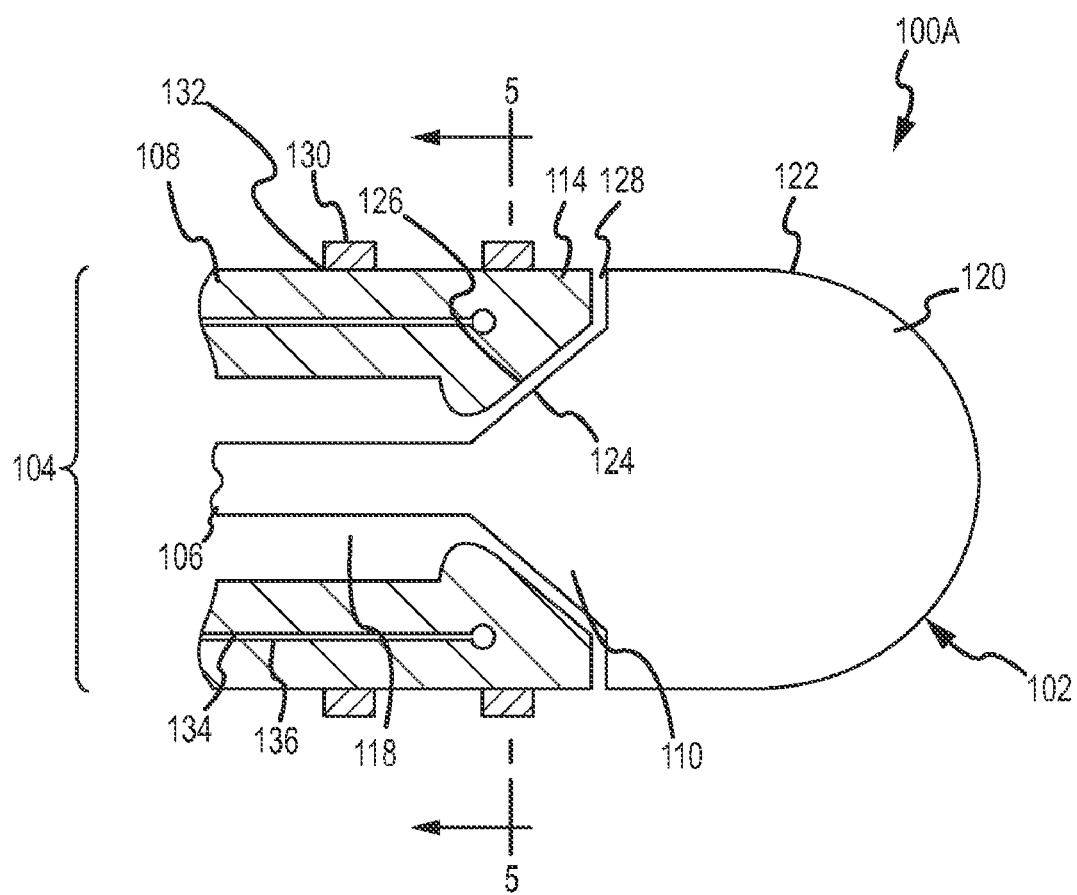
FIG. 4 is a fragmentary view in partial cross-section of a first embodiment of an ablation catheter assembly with a front-loaded catheter tip according to the invention.

In accordance with a first embodiment of the instant invention, FIG. 4 illustrates an ablation catheter assembly 100A. A catheter assembly provided in accordance with the teachings of the present invention can be used in various therapeutic and/or diagnostic applications, such as the performance of a cardiac ablation procedure and other similar applications/procedures. Accordingly, one of ordinary skill in the art will recognize and appreciate that the inventive catheter can be used in any number of therapeutic and/or diagnostic applications. The catheter assembly of the invention can be used for, among other things, ablation procedures on a human heart. The catheter assembly 100A includes a catheter 102 comprising an elongate catheter shaft assembly 104 having an inner shaft member 106 disposed within an outer shaft member 108. The inner shaft member 106 has a distal end 110 and a proximal end 112 (see FIG. 6). The outer shaft member 108 has a distal end 114, a proximal end 116 (see FIG. 6), and a lumen 118 between the distal end 114 and the proximal end 116. The inner shaft member 106 can be inserted into the lumen 118 of the outer shaft member 108 along a longitudinal direction of the elongate catheter shaft assembly. The inner shaft member 106 includes at the distal end 110 thereof a front-loaded catheter tip member 120 having a lateral dimension that is larger than a lateral dimension of the lumen 118 of the outer shaft member 108. The catheter tip member 120 has an outer surface 122. In an embodiment, the catheter tip member 120 can be cap-shaped. The catheter tip member 120 can be coupled or connected to or can be of a unitary construction with the inner shaft member 106. The inner shaft member 106 can have a sloped, angled or stepped portion 124. The outer shaft member 108 can have a sloped, angled or stepped portion 126 that corresponds to the sloped, angled or stepped portion 124 of the inner shaft member 106. The inner shaft member 106 can be separate from the outer shaft member 108. The separate configuration of the inner shaft member 106 and the outer shaft member 108 allows the catheter tip member 120 and inner shaft member 106 to freely move with respect to the outer shaft member 108. The distal end 114 of the outer shaft member 108 and the distal end 110 of the inner shaft member 106, including the catheter tip member 120, can be configured to form a fluid-tight connection that is at least substantially free of crevices on an external surface of the connection (see FIG. 15). The catheter tip member 120 preferably has a maximum outer diameter that can be equal in size to an outer diameter of the outer shaft member 108. The inner shaft member 106 having the catheter tip member 120 can be movable with respect to the outer shaft member 108 in the longitudinal direction to adjust a spacing between the distal end 110 of the inner shaft member 106 and the distal end 114 of the outer shaft member 108. A non-zero spacing between the distal end 110 of the inner shaft member 106 and the distal end 114 of the outer shaft member 108 provides a fluid flow path or channel 128 between an interior of the elongate catheter shaft assembly and an exterior of the elongate catheter shaft assembly. The channel 128 can be formed to facilitate irrigated ablation such as saline irrigation. This configuration provides for irrigation and separates the fluid flow paths from electrodes or electrically active elements. In an embodiment, the inner shaft member including the catheter tip member can be inserted into the lumen from the distal end of the outer shaft member to be detachably connected to the outer shaft member, and can be removable out of the lumen from the distal end of the outer shaft member.

The catheter tip member may, without limitation, be constructed of a metal material having a high thermal conductivity, such as steel, silver, gold, chromium, aluminum, molybdenum, tungsten, nickel, platinum or another suitable metal material. The catheter shaft assembly may, for example, be constructed of a flexible polymeric material, such as polyurethane, nylon, polyethylene, various types of plastic materials, such as PEBAX, or other suitable polymeric materials. (PEBAX is a registered trademark of Arkema France of France.) The catheter shaft assembly can also include a metal braided or coiled internal element (not shown) to provide additional torque transfer capabilities, pressure resistance, and/or tensile strength to the shaft. Additionally, the catheter tip member and catheter shaft assembly can be formed using any number of different manufacturing processes known in the art including, without limitation, extrusion processes. In an embodiment, the length of the inner shaft member can be from about 75 cm (centimeters) to about 150 cm. Similarly, in an embodiment, the length of the outer shaft member can be from about 75 cm to about 150 cm.

Catheter assemblies in accordance with the teachings of the invention provide an opportunity to employ a larger tip than can be used with a standard catheter assembly having an introducer or sheath. Among other things, the present invention provides a catheter assembly in which the catheter tip member can have a maximum outer diameter that can be equal to the outer diameter of the outer shaft member. In an embodiment, the proximal portion of the inner shaft member has a size of about 4 FR to about 5 FR, while the catheter tip and outer shaft member preferably have a size of about 7 FR to about 8 FR. The inner shaft member can have a sloped, angled, or stepped portion that results in a smaller size of the inner shaft member. Such a configuration can lessen the possibility of trauma to a heart and, for example, trauma to the fossa ovalis when a transseptal puncture is made, by permitting the overall catheter assembly size to be smaller than standard catheter assembly sizes for a given diameter of the catheter tip. In addition, the inner shaft member can be slimmer and smaller than the outer shaft member, and thus there is more space and less contact between the inner shaft member and the outer shaft member. Thus, the ability to freely manipulate the inner shaft member can be increased, and the ability to freely manipulate and move the inner shaft member and catheter tip with respect to the outer shaft member can be improved. This also can provide greater independent degrees of freedom of movement on the other side of a transseptal puncture. Although the outer shaft member is essentially acting like a sheath or introducer, unlike typical sheaths or introducers of standard ablation catheters, the catheter tip member can have a maximum outer diameter that can be equal to the outer diameter of the outer shaft member. This can provide for overall easier movement of the catheter assembly when being maneuvered in a restricted vasculature area.

The catheter assembly of the invention further includes an electrically active element. Preferably, the catheter tip member can include at least one electrically active element. The electrically active element can comprise one or more ablation electrodes, one or more sensing electrodes, an electrical sensor, an electromagnetic element, or another suitable electrically active element. As shown in FIG. 4, the electrically active element can be in the form of a plurality of sensing electrodes 130 disposed on and spaced along an external surface 132 of the outer shaft member 108. The sensing electrodes 130 can be in the form of rings, spots, pads, or other suitable configurations. The sensing electrodes 130 can comprise spaced ring electrodes, such as mapping electrodes, mounted on or affixed to an external surface of the outer shaft member 108. The ring electrodes can be in electrical isolation from the catheter tip. The active outer surface of each sensing electrode 130 can be configured for exposure to blood and/or tissue. The sensing electrodes 130 can be assembled with the catheter, and in particular, on the outer shaft member 108, using any number of known processes. For instance, the sensing electrodes 130 can be built onto the shaft using a reflow process. In such a process, the sensing electrodes 130 can be placed at the desired locations on the outer shaft member, and then the catheter shaft can be exposed to a heating process in which the sensing electrodes 130 and the outer shaft member become affixed or bonded together. The catheter assembly 100A can further include one or more actuation elements 134. The actuation elements 134 can be positioned within an internal portion 136 of the outer shaft member 108. The actuation element 134 can be in the form of one or more pull wires made of a thin conductive metal and designed to deflect and steer the catheter shaft. The pull wire can be surrounded by a liner (not shown) that serves the dual purpose of providing a lubricious surface to allow for the sliding of the pull wire, while also insulating the pull wire from electrical wires (e.g., electrode wires) in the internal portion of the catheter assembly. If provided, the liner can be constructed of a polymeric material, such as polytetrafluoroethylene (PTFE), or any other suitable material. It should be noted that the catheter assembly can include one, two, or more pull wires disposed within the catheter shaft, and more particularly, within the outer shaft member, to enable the distal end to deflect in two or more directions. The catheter assembly can be configured such that various components required for performing the particular functionality of the catheter (e.g., ablation, etc.) are disposed therein, such as electrode wires, shape wires, planarity wires, wiring for temperature sensing elements, and other suitable components. It should be noted that while the embodiments described herein include components that can be primarily used for therapeutic and diagnostic applications, components for various other medical applications using such catheters can also be disposed within the catheter assembly.

Figure 5:
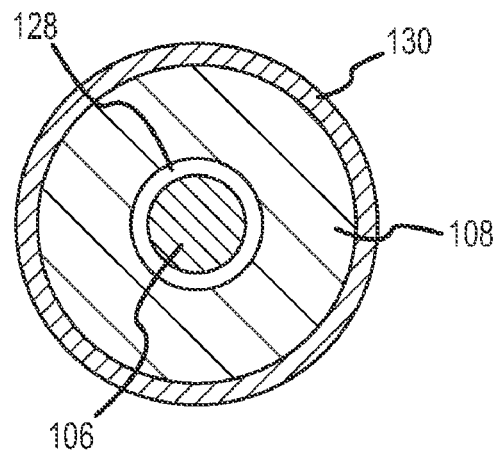
FIG. 5 is a cross-sectional view, taken along line 5-5 of FIG. 4, of the catheter shaft of FIG. 4.

FIG. 5 is a cross-sectional view, taken along line 5-5 of FIG. 4, of the catheter shaft assembly of FIG. 4. FIG. 5 shows the sensing electrode 130, the outer shaft member 108, the channel 128, and the inner shaft member 106. It should be noted that while a cross-sectional profile is illustrated with particularity, the present invention is not so limited. Rather, those of ordinary skill in the art will recognize and appreciate that the catheter assembly can have any number of cross-sectional profiles. Different members of the catheter assembly can have different cross-sectional profiles.

Figure 6:
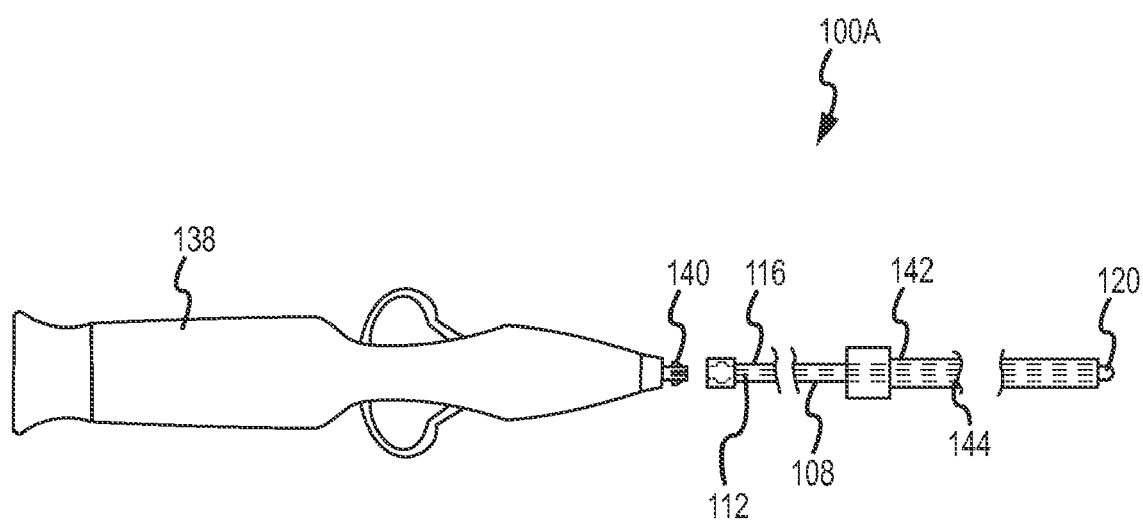
FIG. 6 is a fragmentary view of an embodiment of the ablation catheter assembly of the invention showing a proximal end of the catheter assembly with a first embodiment of a connector element.
Figure 7:
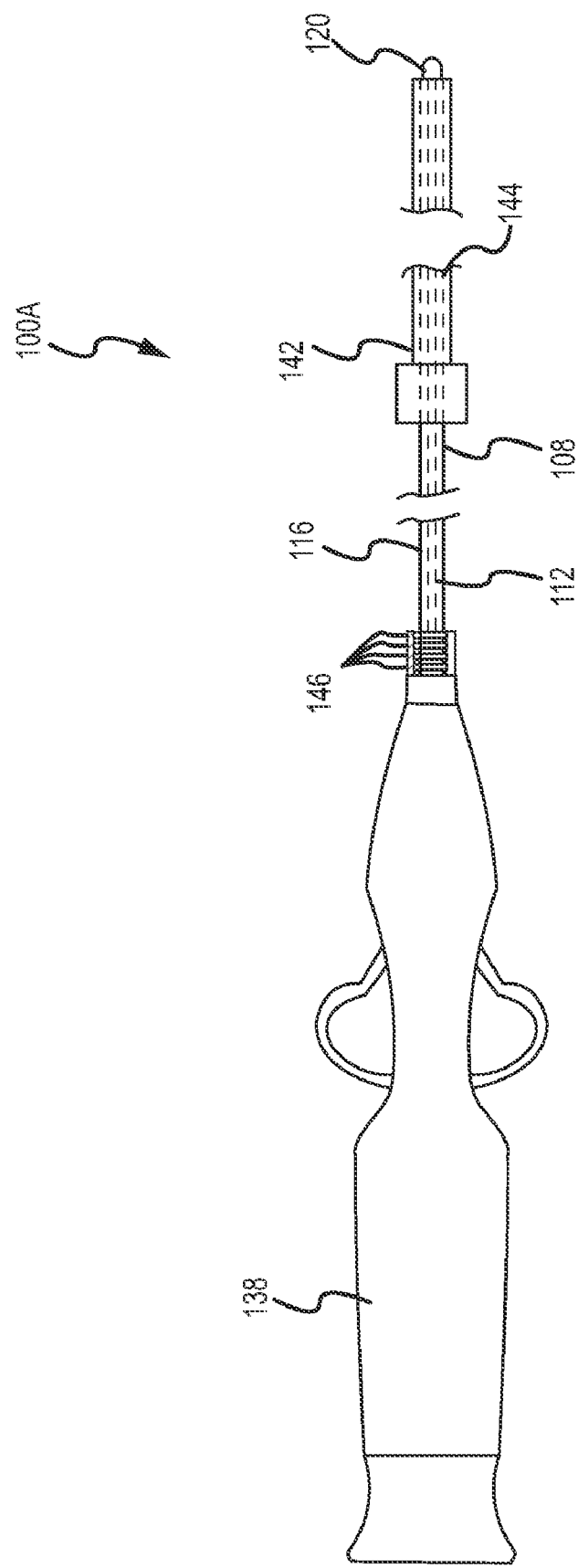
FIG. 7 is a fragmentary view of an embodiment of the ablation catheter assembly of the invention showing a proximal end of the catheter assembly with a second embodiment of a connector element.
Figure 8:
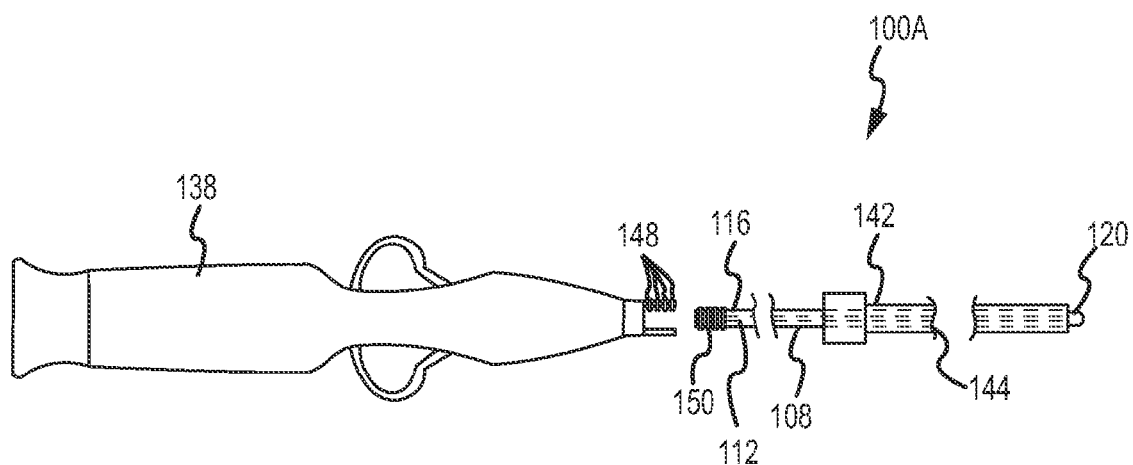
FIG. 8 is a fragmentary view of an embodiment of the ablation catheter assembly of the invention showing a proximal end of the catheter assembly with a third embodiment of a connector element.

FIG. 6 shows a fragmentary view of ablation catheter assembly 100A of the invention showing both the proximal and distal ends of the catheter assembly. FIG. 6 shows the proximal end 112 of the inner shaft member and the proximal end 116 of the outer shaft member. A handle member 138 can be positioned at the proximal end of the catheter assembly and adapted for connection to the catheter assembly. The handle member 138 can further be adapted for connection to the actuation elements so that a user of the catheter assembly can selectively manipulate the distal end of the catheter assembly to deflect in one or more directions (e.g., up, down, left, and right). The handle can be operative to effect movement (i.e., deflection) of the distal end of the catheter assembly. FIG. 6 shows the handle member 138 having an electrical connector element in the form of a quick connect 140. The electrical connector element can be used to make an electrical connection to the sensing electrodes at the distal end of the catheter assembly. The catheter assembly can further comprise an electrical line (see FIG. 14) coupled between the electrical connector at the proximal end of the elongate catheter shaft assembly and the catheter tip at the distal end of the catheter having the electrically active element, such as the electrodes. The electrically active element can be activated by electrical energy supplied through the electrical connector at the proximal end of the catheter assembly via the electrical line to the catheter tip at the distal end of the catheter assembly. The elongate catheter shaft assembly can include a sheath 142 having a sheath lumen 144. The outer shaft member 108 can be inserted into the sheath lumen 144. The sheath 142 can include another actuation mechanism or element to provide additional steering capabilities for the catheter assembly. FIG. 7 shows a fragmentary view of ablation catheter assembly 100A of the invention showing the catheter assembly having the sheath 142, sheath lumen 144, and handle member 138 adapted for connection to the catheter assembly. FIG. 7 shows the handle member having an electrical connector element in the form of a plurality of spring-loaded contacts 146. FIG. 8 shows a fragmentary view of ablation catheter 100A of the invention showing the catheter assembly having the sheath 142, sheath lumen 144, and handle member 138 adapted for connection to the catheter assembly. FIG. 8 shows the handle member 138 adapted for connection to the catheter assembly. FIG. 8 shows the handle member having an electrical connector element in the form of a plurality of set screws 148 that are manually driven to make contact with electrical or ring contacts 150. Alternatively, the electrical connector element can comprise a grounding pad, a clamp connector, a snap around connector with crown pins, or another suitable electrical connector element.

Figure 9:
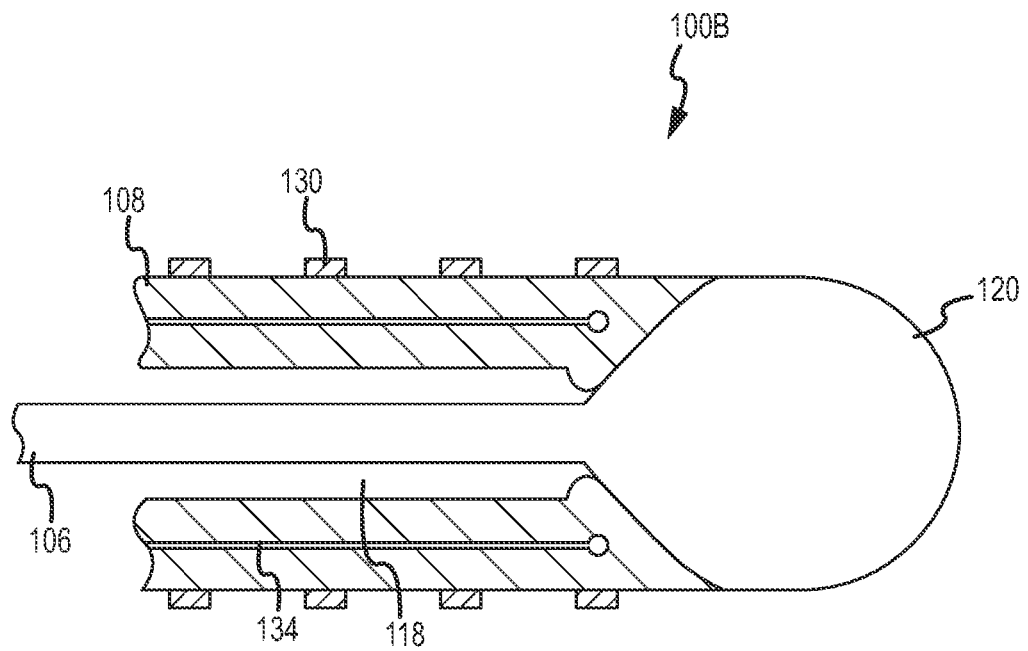
FIG. 9 is a fragmentary view in partial cross-section of a second embodiment of an ablation catheter assembly with a front-loaded catheter tip in an unextended position.
Figure 10:
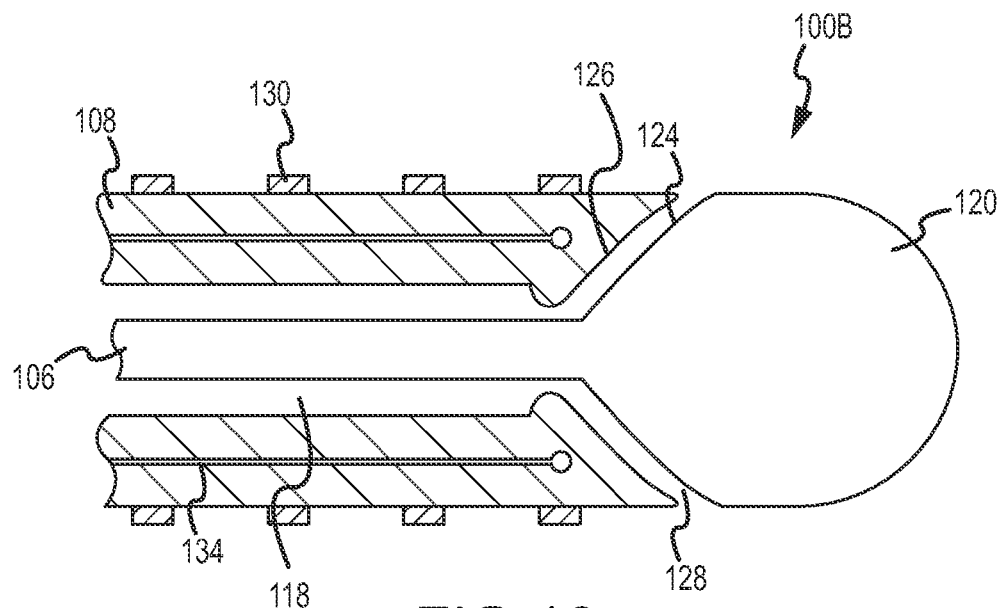
FIG. 10 is a fragmentary view in partial cross-section of the ablation catheter assembly of FIG. 9 in a partially extended position.

FIG. 9 shows a fragmentary view in partial cross-section of a second embodiment of an ablation catheter assembly 100B with front-loaded catheter tip 120 in an unextended position. The catheter assembly 100B of this embodiment shows the distal end 110 of the inner shaft member 106 and the distal end 114 of the outer shaft member 108 in a varied configuration from the catheter assembly 100A of FIG. 4. FIG. 10 shows a fragmentary view in partial cross-section of the ablation catheter assembly 100B of FIG. 9 in a partially extended position. When the catheter tip 120 and inner shaft member 106 are extended from the outer shaft member 108, the channel 128 can be formed to facilitate irrigated ablation such as saline irrigation or heparinized saline irrigation. The configuration of this embodiment promotes saline flow around the catheter tip when the catheter assembly is in a partially extended or fully extended position. This configuration effectively keeps the saline or heparinized saline in contact with the catheter tip. The catheter tip can be an ablation electrode, and irrigation of the ablation electrode reduces or prevents thrombus formation.

Figure 11:
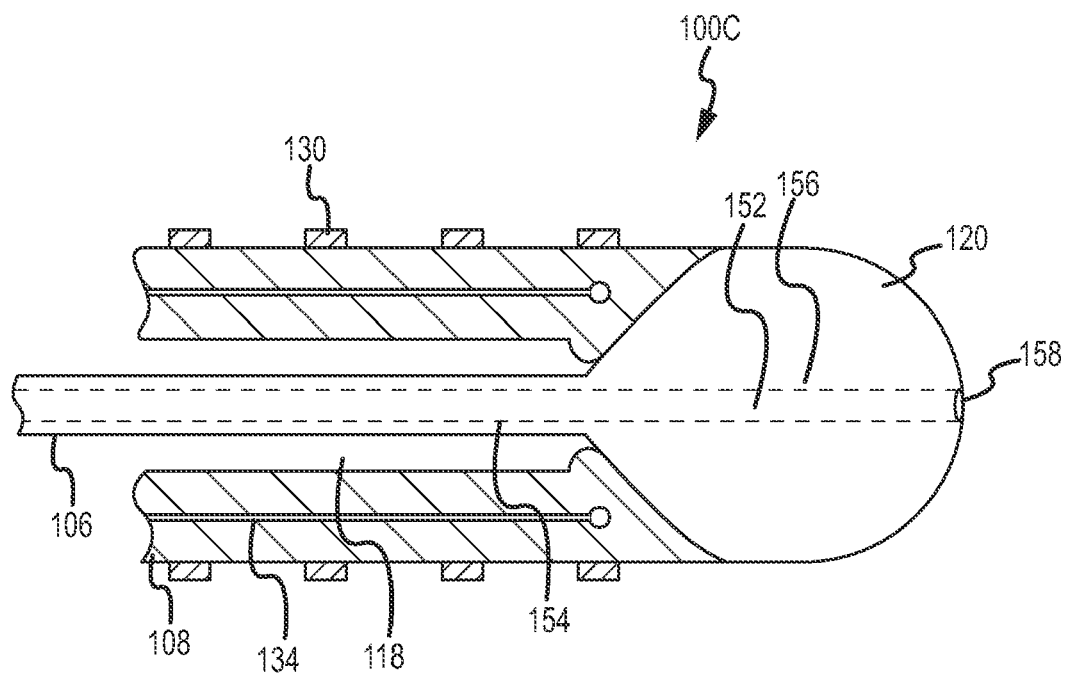
FIG. 11 is a fragmentary view in partial cross-section of a third embodiment of an ablation catheter assembly with a front-loaded catheter tip having an internal lumen and being in an unextended position.
Figure 12:
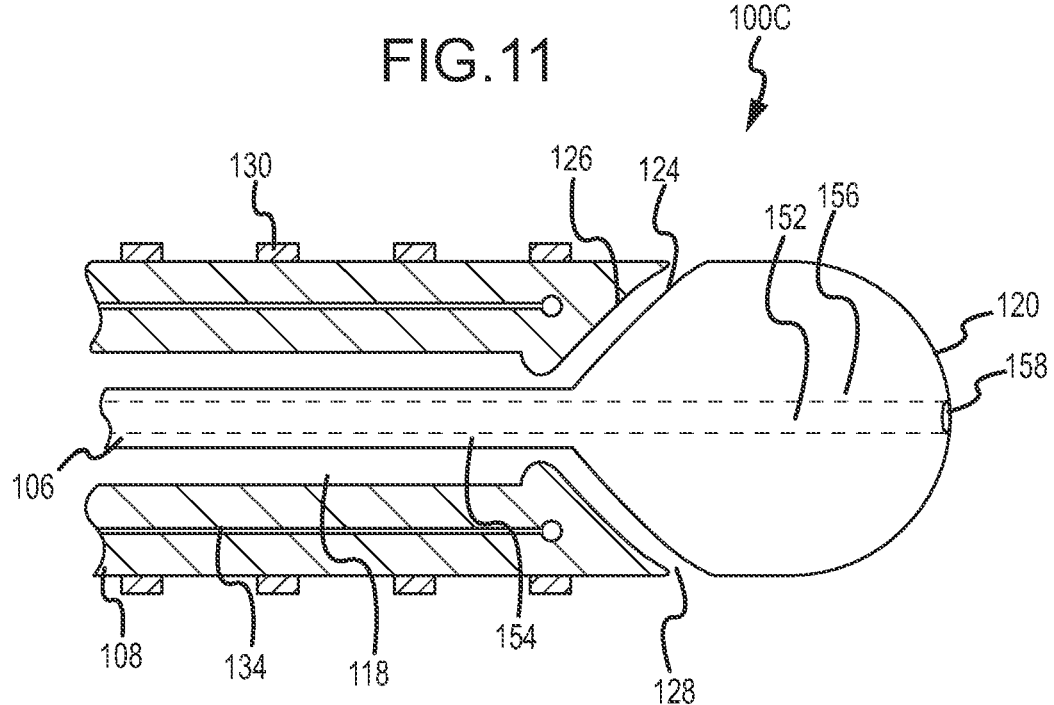
FIG. 12 is a fragmentary view in partial cross-section of the ablation catheter assembly of FIG. 11 in a partially extended position.

FIG. 11 shows a fragmentary view in partial cross-section of a third embodiment of an ablation catheter assembly 100C with front-loaded catheter tip member 120 having a similar configuration to the ablation catheter assembly 100B in FIGS. 9-10. However, in this embodiment, the catheter assembly 100C includes an internal lumen 152 longitudinally extending through an internal portion 154 of the inner shaft member 106 and through an internal portion 156 of the catheter tip member 120 to form an opening 158 at the catheter tip member 120. Depending upon the intended application of the catheter assembly 100C, the internal lumen 152 can extend the entire length of the inner shaft member 106 and the catheter tip member 120 or can extend less than the entire length. Additionally, the catheter assembly 100C can include one or more lumens in the inner shaft member and/or the outer shaft member. Therefore, one of ordinary skill in the art will recognize and appreciate that the inner shaft member and/or outer shaft member can have one or more lumens and/or can have a lumen or lumens of various lengths. It should be noted that both the foregoing and the following descriptions relating to the lumen or lumens apply with equal force to both single and multi-luminal arrangements. FIG. 11 shows the catheter assembly 100C in an unextended position. FIG. 12 shows a fragmentary view in partial cross-section of the ablation catheter assembly 100C of FIG. 11 in a partially extended position. When the catheter tip member 120 and inner shaft member 106 are extended from the outer shaft member 108, the channel 128 (see FIG. 12) can be formed to facilitate irrigated ablation such as saline irrigation or heparinized saline irrigation. The configuration of this embodiment promotes saline flow around the catheter tip when the catheter assembly is in a partially extended or fully extended position. This configuration effectively keeps the saline or heparinized saline in contact with the catheter tip. In addition, saline or heparinized saline can also flow through the internal lumen 152 to facilitate irrigated ablation. Such additional flow through the internal lumen keeps the saline or heparinized saline in contact with the catheter tip member and helps to reduce or prevent thrombus and charring at the catheter tip.

Figure 13:
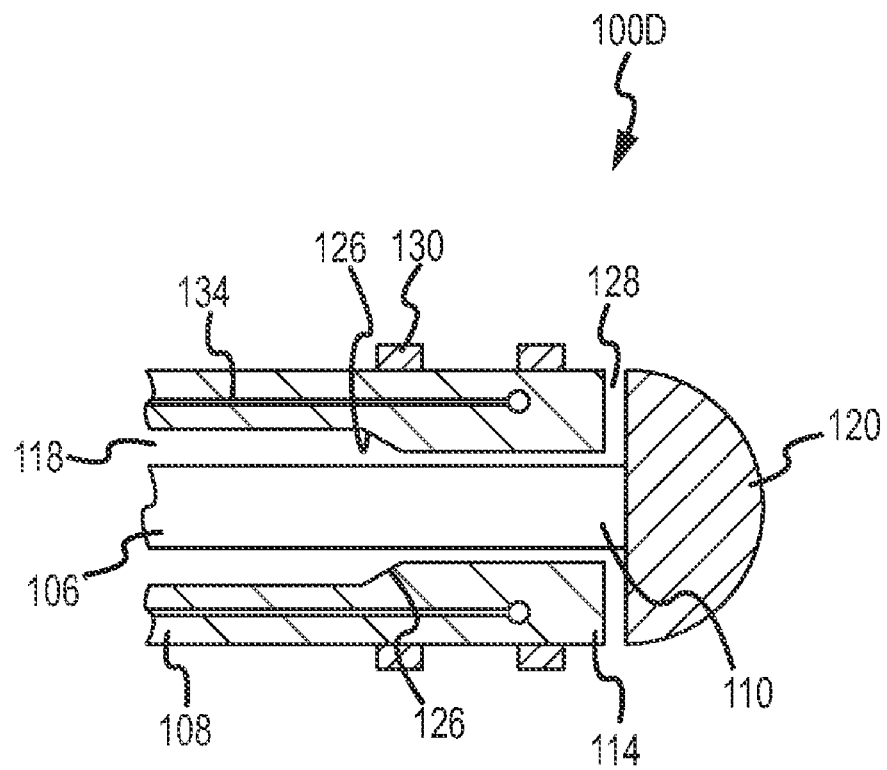
FIG. 13 is a fragmentary view in partial cross-section of a fourth embodiment of an ablation catheter assembly with a front-loaded catheter tip in a partially extended position.

FIG. 13 shows a fragmentary view in partial cross-section of a fourth embodiment of an ablation catheter assembly 100D in a partially extended position and having the front-loaded catheter tip 120, the inner shaft member 106, the outer shaft member 108, sensing electrodes 130, and actuation elements 134. In this embodiment, the configuration of the distal end 114 of the outer shaft member 108 is varied from the distal end of the outer shaft member shown in FIGS. 4 and 9-12, and the inner shaft member 106 can be elongated and substantially straight. The inner shaft member 106 can have a constant outer diameter. The outer shaft member 108 can have sloped, angled or stepped portion 126. The catheter tip member 120 can be coupled or connected to or in a unitary configuration with the inner shaft member 106. The catheter tip member 120 can be separate from and adapted to fit at a right angle adjacent to the distal end 114 of the outer shaft member 108.

Figure 14:
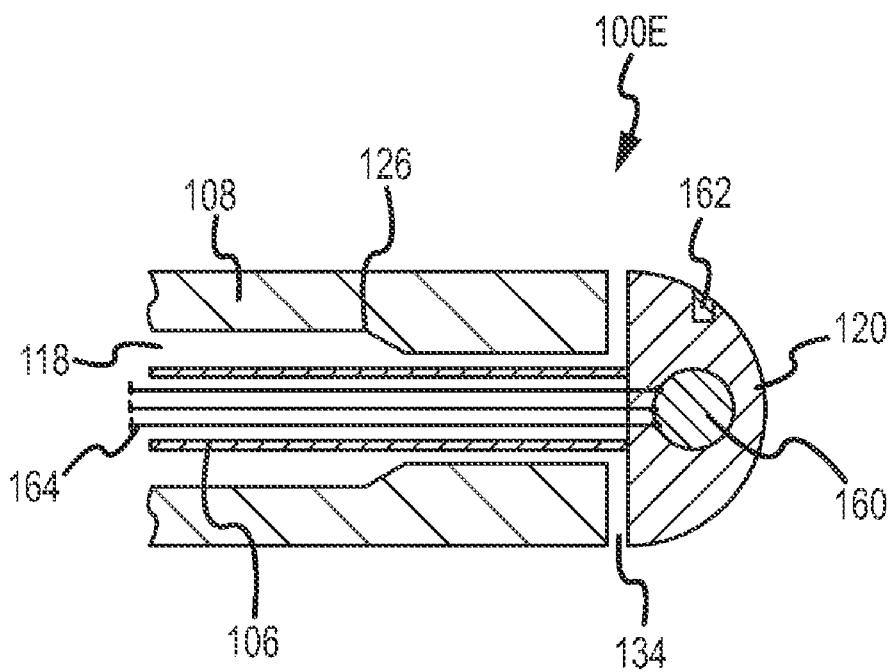
FIG. 14 is a fragmentary view in partial cross-section of a fifth embodiment of an ablation catheter assembly with a front-loaded catheter tip having a magnetic material in the tip and being in a partially extended position.

FIG. 14 shows a fragmentary view in partial cross-section of a fifth embodiment of an ablation catheter assembly 100E with the front-loaded catheter tip member 120, the inner shaft member 106, and the outer shaft member 108. This embodiment can or can not include sensing electrodes on the outer shaft member. This catheter assembly embodiment has a catheter tip member 120 that includes a magnetic material or element 160 and can include at least one thermocouple element 162 mounted within or affixed to the catheter tip member 120. The magnetic material can comprise a permanent magnet, an electromagnetic element, a ferromagnetic material, or another suitable magnetic material. The catheter assembly of this embodiment can further include a plurality of electrical lines or wires 164 that can be disposed within the interior of the inner shaft member 108 and that can extend to and connect with the magnetic material 160. Such magnetic material can be used in addition to, or in place of, the sensing electrodes 130 (see FIG. 13). The magnetic material 160 can be disposed at the extreme distal end of the catheter tip member 120. The magnetic material 160 can be configured for various functionality and can be affixed to the catheter tip member 120 in a number of ways. For instance, the magnetic material 160 can be bonded to the interior of the catheter tip using an epoxy material or can be affixed in another suitable manner. The electrical connector elements as shown in FIGS. 6-8 can also be used with the embodiment shown in FIG. 14. Similar to the embodiment of FIG. 13, in the embodiment of FIG. 14, the inner shaft member 106 can be elongated and substantially straight. The inner shaft member 106 can have a constant outer diameter. The outer shaft member 108 can have sloped, angled or stepped portion 126. The catheter tip member 120 can be coupled or connected to or in a unitary configuration with the distal end of the inner shaft member 106. The catheter tip member 120 can be separate from and adapted to fit at a right angle adjacent to the distal end 114 of the outer shaft member 108. The magnetic material 160 in the catheter tip member 120 is magnetically driven by an external magnetic field. The catheter tip element 120 can be an ablation electrode that is magnetically driven to the target tissue for ablation.

Figure 15:
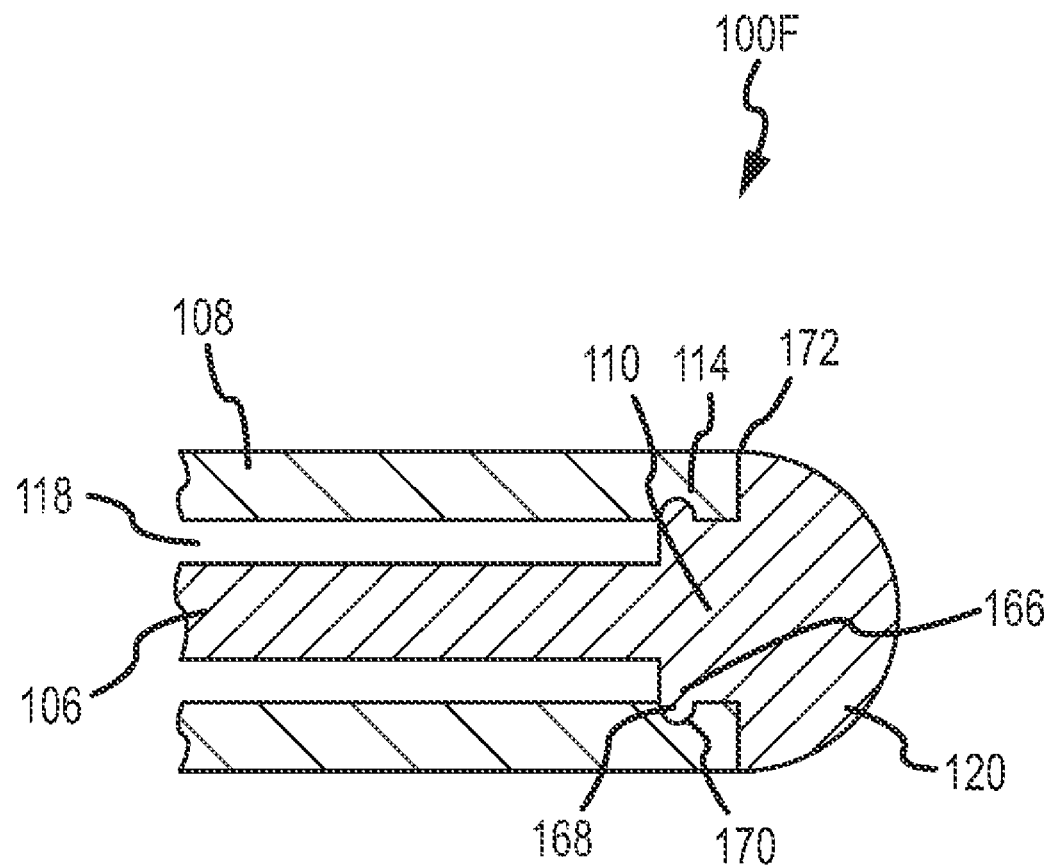
FIG. 15 is a fragmentary view in partial cross-section of a sixth embodiment of an ablation catheter assembly with a front-loaded catheter tip having a snap-fit connection.

FIG. 15 is a fragmentary view in partial cross-section of a sixth embodiment of an ablation catheter assembly 100F with the front-loaded catheter tip member 120, the inner shaft member 106, the outer shaft member 108, and the lumen 118. In this embodiment, there is provided between the distal end 114 of the outer shaft member 108 and the distal end 110 of the inner shaft member 106 a snap-fit connection 166 comprising a protruding portion 168 and a receiving portion 170 adapted to receive the protruding portion 168. The protruding portion 166 can be formed on the inner shaft member 106, and the receiving portion 168 can be formed in the outer shaft member 108. The snap-fit connection can also be in the form of other suitable configurations. In this embodiment, the distal end 114 of the outer shaft member 108 and the distal end 110 of the inner shaft member 106 including the catheter tip member 120 are configured with the snap-fit connection to form a fluid-tight connection that is at least substantially free of crevices on an external surface 172 of the connection. Such fluid-tight connection can help to reduce or prevent thrombus formation. In this embodiment, the inner shaft member 106 and the outer shaft member 108 are not configured to be separable after the snap-fit connection is made. The catheter tip member 120 can be coupled or connected to or in a unitary configuration with the inner shaft member 106.

Figure 16:
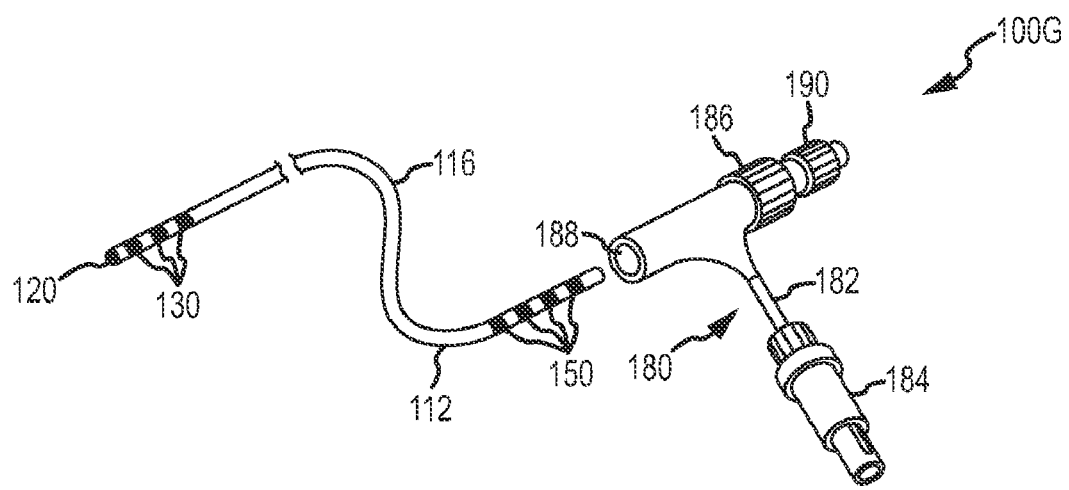
FIG. 16 shows a fragmentary view of ablation catheter assembly of the invention.
Figure 17:
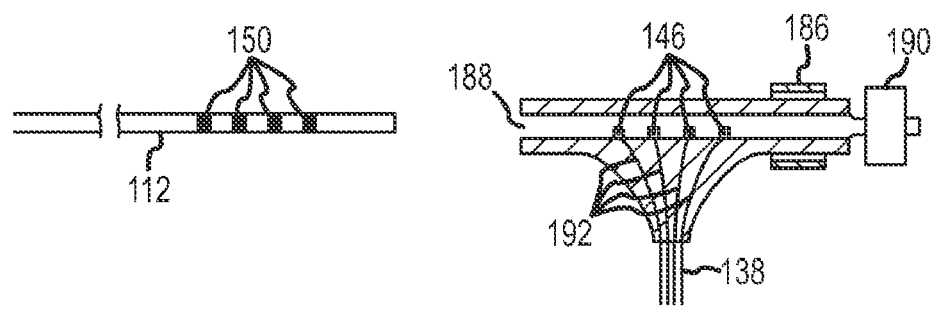
FIG. 17 shows a fragmentary view of a catheter assembly of the invention.
Figure 18:
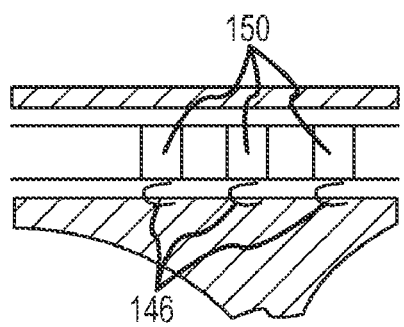
FIG. 18 shows a fragmentary view of the catheter assembly in cross-section.
Figure 19:
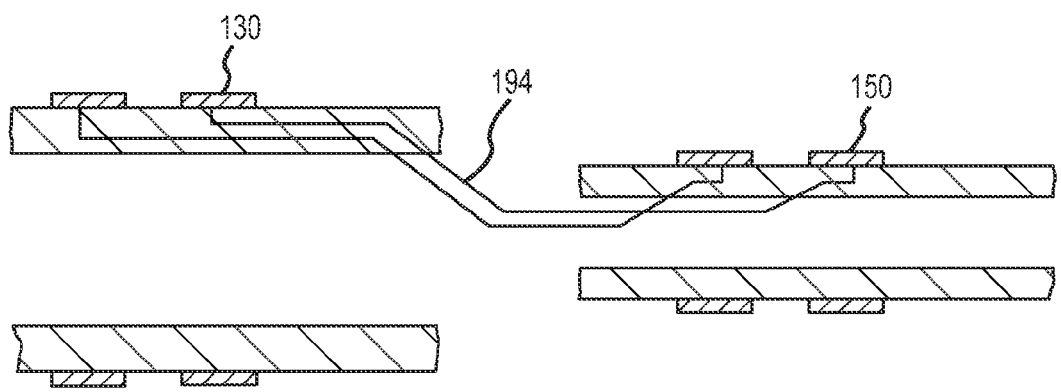
FIG. 19 is a fragmentary view of the catheter assembly of FIG. 16 showing an electrical line coupled between electrodes on the outer and inner shaft members.

FIG. 16 shows a fragmentary view of ablation catheter assembly 100G of the invention showing both the proximal and distal ends of the catheter assembly. FIG. 16 shows the proximal end 112 of the inner shaft member and the proximal end 116 of the outer shaft member. Sensing electrodes 130 are shown on the distal end of the outer shaft member and catheter tip member 120 is shown on the distal end of the inner shaft member. A handle member 138 can be positioned at the proximal end of the catheter assembly and adapted for connection to the catheter assembly, as shown. In the embodiment shown in FIG. 16, the handle member 138 is further adapted to have a connecting member 180 to a power supply having a lumen 182 that houses a plurality of electrical lines or electrical wires that connect to the power supply. The connecting part 180 is configured to operably interact with an electrical connector 184. The electrical connector 184 can be, for example, a LEMO® connector (LEMO; Rohnert Park, Calif.) or a Hypertronics Corp. connector (Hypertronics Corp.; Hudson; MA). The handle member 138 can further be adapted to include a tubing adapter 186 and fitting 190 that allows for connecting the catheter 100G to tubing to the catheter for supplying irrigated catheters with saline or heparinized saline. In one embodiment, the adapter 186 is a Tuohy Borst adapter. The fitting 190 can be a Luer fitting. FIG. 16 shows the handle member 138 having a catheter receptacle 188. The catheter receptacle can be used to make an electrical connection to an electrode 150, shown here as a plurality of electrodes at the proximal end of the catheter assembly. The catheter assembly can further comprise an electrical line or wire (see FIG. 14, 164) coupled between the electrical connector at the proximal end of the elongate catheter shaft assembly and the catheter tip member 120 at the distal end of the catheter having the electrically active element, such as electrodes. In some embodiments, there are a plurality of electrical lines or wires to an electrode to allow, for example, multiple resistance measurements. The electrically active element can be activated by electrical energy supplied through the electrical connector at the proximal end of the catheter assembly via the electrical line to the catheter tip at the distal end of the catheter assembly. Referring to FIG. 19, an electrical line or wire 194 can also be coupled between a sensing electrode 130 on the outer shaft member of catheter 100G and a corresponding electrode 150 on the proximal end 112 of the inner shaft member of catheter 100G FIG. 17 shows a fragmentary view of a catheter assembly, showing the handle member 138 in partial cross-section, showing the inner lumen of the electrical connector element receptacle 188. The electrical connector element receptacle 188 has an electrical connector element in the form of a plurality of contacts 146 that are in electrical contact with a power supply. When the proximal end 116 of the catheter assembly 100G is inserted into the electrical connector element receptacle 188, the proximal electrodes 150 contact the electrical connector element sufficiently to conduct electrical energy; this is illustrated in FIG. 18.

The plurality of contacts 146 can be any number sufficient to conduct the necessary electrical energy to perform an ablation procedure. For example, the plurality of contacts 146 can be from 2 to 20, specifically, 2, 3, 4, 5, 6, 7, 8, 9, 10, 15, or 20 contacts. Likewise, the plurality of proximal electrodes 150 can also likewise vary; that is from 2 to 20, specifically, 2, 3, 4, 5, 6, 7, 8, 9, 10, 15, or 20 contacts. The plurality of contacts 146 and the plurality of proximal electrodes can be the same; in other embodiments, the plurality of contacts 146 is greater than the plurality of proximal electrodes to allow connecting of additional items, such as, for example, temperature-sensing circuit. The plurality of contacts 146 can be flexible to accommodate changes in catheter size during use. For example, the plurality of contacts 146 can be spring-loaded contacts. In some embodiments, a user manipulates each member of the plurality of contacts 146 or jointly to make contact with the proximal electrodes 150.

Although a number of representative embodiments according to the present teachings have been described above with a certain degree of particularity, those skilled in the art could make numerous alterations to the disclosed embodiments without departing from the scope of this invention. For example, different types of catheters can be manufactured or result from the inventive process described in detail above. For instance, catheters used for diagnostic purposes and catheters used for therapeutic purposes can both be manufactured using the inventive process. Additionally, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the invention as defined in the appended claims.

What is claimed is:

1. A catheter comprising:
   (a) an elongate catheter shaft assembly having an inner shaft member having a distal end and a proximal end, and an outer shaft member having a distal end, a proximal end, and a lumen between the distal end and the proximal end thereof, the inner shaft member being inserted into the lumen of the outer shaft member along a longitudinal direction of the elongate catheter shaft assembly, wherein the inner shaft member includes at the distal end thereof a catheter tip member having a lateral dimension that is larger than a lateral dimension of the lumen of the outer shaft member, and
   (b) at least one electrode at least partially disposed on an external surface of the outer shaft member;
   (c) an electrical line coupled between the at least one electrode of the outer shaft member and an electrode disposed on an external surface of the inner shaft member at the proximal end; and
   (d) a handle member at the proximal end of the assembly having a catheter receptacle, wherein when the proximal end of the inner shaft member is inserted into the catheter receptacle, the electrode on the external surface of the inner shaft member electrically contacts an electrical connector element.

2. The catheter of claim 1, wherein the electrode on the external surface of the inner shaft member electrically contacts an electrical connector element internally.

3. The catheter of claim 1, wherein the electrode on the external surface of the inner shaft member electrically contacts an electrical connector element externally.

4. The catheter of claim 1, wherein the electrical connector element comprises a plurality of contacts.

5. The catheter of claim 1, wherein the plurality of contacts is 2 to 20.

6. The catheter of claim 1 wherein the elongate catheter shaft assembly includes a sheath having a sheath lumen, and wherein the outer shaft member is inserted into the sheath lumen.

7. The catheter of claim 1, wherein the distal end of the outer shaft member and the distal end of the inner shaft member including the catheter tip member are configured to form a fluid-tight connection that is at least substantially free of crevices on an external surface of the connection.

8. The catheter of claim 1, wherein the outer shaft member has an outer diameter, and wherein the catheter tip member has a maximum outer diameter that is equal to the outer diameter of the outer shaft member.

9. The catheter of claim 1, wherein the at least one electrically active element is selected from the group consisting of an ablation electrode, a sensing electrode, an electrical sensor, and an electromagnetic element.

10. The catheter of claim 1, wherein the outer shaft member includes one or more actuation elements to steer the elongate catheter shaft assembly.

11. The catheter of claim 1, wherein the inner shaft member having the catheter tip member is movable with respect to the outer shaft member in the longitudinal direction to adjust a spacing between the distal end of the inner shaft member and the distal end of the outer shaft member.

12. The catheter of claim 1, wherein a non-zero spacing between the distal end of the inner shaft member and the distal end of the outer shaft member provides a fluid flow path between an interior of the elongate catheter shaft assembly and an exterior of the elongate catheter shaft assembly.

13. The catheter of claim 12, wherein the handle member is configured to provide a fluid path from the handle member to the fluid flow path between the interior of the elongate catheter shaft assembly and the exterior of the catheter shaft assembly.

14. A catheter comprising:
(a) an elongate catheter shaft assembly including an inner shaft member having a distal end and a proximal end, and an outer shaft member having a distal end, a proximal end, and a lumen between the distal end and the proximal end thereof, the inner shaft member being inserted into the lumen of the outer shaft member along a longitudinal direction of the elongate catheter shaft assembly, the inner shaft member extending at least substantially through an entire length of the lumen of the outer shaft member, wherein the inner shaft member includes at the distal end thereof a catheter tip member having a lateral dimension that is larger than a lateral dimension of a lumen of the outer shaft member,
(b) at least one electrode disposed on an external surface of the outer shaft member;
(c) an electrical line coupled between the at least one electrode of the outer shaft member and an electrode disposed on an external surface of the inner shaft member at the proximal end; and
(d) a handle member at the proximal end of the assembly having a catheter receptacle, wherein when the proximal end of the inner shaft member is inserted into the catheter receptacle, the electrode on the external surface of the inner shaft member electrically contacts an electrical connector element.

15. The catheter of claim 14, wherein the electrical connector element comprises a plurality of contacts.

16. The catheter of claim 15, wherein the plurality of contacts is 2 to 20.

17. The catheter of claim 15, wherein the distal end of the outer shaft member and the distal end of the inner shaft member including the catheter tip member are configured to form a fluid-tight connection that is at least substantially free of crevices on an external surface of the connection.

18. The catheter of claim 15, wherein the outer shaft member has an outer diameter, and wherein the catheter tip member has a maximum outer diameter that is equal to the outer diameter of the outer shaft member.

19. The catheter of claim 15, wherein the catheter tip member includes at least one electrically active element.

20. The catheter of claim 15, wherein the inner shaft member having the catheter tip member is movable with respect to the outer shaft member in the longitudinal direction to adjust a spacing between the distal end of the inner shaft member and the distal end of the outer shaft member.

21. The catheter of claim 15, wherein a non-zero spacing between the distal end of the inner shaft member and the distal end of the outer shaft member provides a fluid flow path between an interior of the elongate catheter shaft assembly and an exterior of the elongate catheter shaft assembly.

22. The catheter of claim 21, wherein the handle member is configured to provide a fluid path from the handle member to the fluid flow path between the interior of the elongate catheter shaft assembly and the exterior of the catheter shaft assembly.

* * * * *